United States Patent [19]
Gallo

[11] Patent Number: 5,249,389
[45] Date of Patent: Oct. 5, 1993

[54] TOOL FOR REMOVING POLLEN FROM LILIES

[76] Inventor: Joseph S. Gallo, 937 East St., Walpole, Mass. 02081

[21] Appl. No.: 896,234

[22] Filed: Jun. 10, 1992

[51] Int. Cl.$^5$ .......................... A01G 7/00; A01H 1/02
[52] U.S. Cl. ..................................... 47/1.41; 47/1.5; 47/1.01; 294/99.2
[58] Field of Search ............... 47/1.01, 1.41, 1.5; 294/99.2; 606/133, 210

[56] References Cited

U.S. PATENT DOCUMENTS

| | | | |
|---|---|---|---|
| 789,659 | 5/1905 | Kantorowicz | 47/1.01 |
| 795,013 | 7/1905 | Weiler | 294/99.2 |
| 1,598,514 | 8/1926 | Benner | 47/1.01 |
| 2,683,274 | 7/1954 | Kappes | 294/99.2 |
| 2,908,923 | 10/1959 | Schlechter | 47/1.5 |
| 3,535,822 | 10/1970 | Fruth et al. | 47/1.5 |
| 4,126,962 | 11/1978 | Polcaro . | |
| 4,159,596 | 7/1979 | Downing | 47/1.41 |
| 4,330,936 | 5/1982 | Swarth | 294/99.2 |
| 4,601,690 | 7/1986 | Jacobson | 294/99.2 |
| 4,716,677 | 1/1988 | Moore . | |
| 4,947,580 | 8/1990 | Moore | 47/1.5 |
| 4,955,897 | 9/1990 | Ship | 606/210 |

FOREIGN PATENT DOCUMENTS

| | | | |
|---|---|---|---|
| 198967 | 6/1908 | Fed. Rep. of Germany | 47/1 |
| 718042 | 2/1942 | Fed. Rep. of Germany | 47/1.5 |
| 929758 | 7/1955 | Fed. Rep. of Germany | 47/1.5 |
| 343897 | 6/1904 | France | 47/1 |
| 2603182 | 3/1988 | France | 47/1 R |
| 176837 | 7/1935 | Switzerland | 47/1 |
| 1758 | of 1893 | United Kingdom | 47/1.5 |
| 0058611 | 8/1982 | United Kingdom | 47/1.5 |

*Primary Examiner*—Carl D. Friedman
*Assistant Examiner*—Joanne C. Downs
*Attorney, Agent, or Firm*—Fish & Richardson

[57] ABSTRACT

The pollen-supporting anthers of lilies is removed, without staining the fingers or clothing of the operator, and without spilling pollen in the work area, by using a tweezer fitted at each free end with an anther-contacting member that includes a layer of foam material. The softness of the foam material, permits the anthers, which are held quite loosely on the lily filaments, to break free without pulling away the filaments. The anthers with supported pollen can then be deposited in a waste receptacle, simply by opening the tweezers over the waste receptacle and gently tapping the tweezers on the receptacle.

8 Claims, 2 Drawing Sheets

TOOL FOR REMOVING POLLEN FROM LILIES

BACKGROUND OF THE INVENTION

This invention realtes to the removal of pollen from lilies and similar flowers.

It has long been desirable in preparing floral arrangements including lilies, and when live lily plants are displayed, to remove what are known as the anthers, which are the pollen covered ends of the filaments extending from the lily flower. If not removed, the pollen can come into contact with the clothing or skin of people in the vicinity of the flower, with disagreeable results. Pollen landing on clothing can permanently stain the clothing. Likewise, pollen landing on the skin can be very difficult to remove, leaving the skin an undesirable yellow color.

This problem has existed for those in the floral trade for generations. There have been efforts to solve the problem, but none have been satisfactory. Typically, even today, the anthers are removed by hand, with the result that the floral worker's hands become stained, pollen is spilled onto clothing, and a general mess is made of the workplace. The pistil located in the center of the pattern of filaments and anthers is also a source of difficulty when the anthers are removed by hand, as it contains a sticky outer coating (intended to attract pollen), which if it contacts the hands when the anthers are being removed can be a nuisance. Wooden tweezers have been tried as a means of removing the anthers, but the tweezers have tended to pull out the filaments with the anthers, resulting in a harm to the aesthetic appearance of the lily.

SUMMARY OF THE INVENTION

I have discovered that the anthers can be easily and effectively removed, without staining the fingers or clothing of the operator, and without spilling pollen in the work area, by using a tweezer fitted at each tweezer end with an anther-contacting member that includes a layer of foam material. The softness of the foam material, permits the anthers, which are held quite loosely on the filaments, to break free without pulling away the filaments. The anthers with supported pollen can then be deposited in a waste receptacle, simply by opening the tweezers over the waste receptacle and gently tapping the tweezers on the receptacle.

In preferred embodiments, the anther-contacting member is a multi-layer composite that includes both the layer of foam material and a layer of bristles that overlies the foam layer with the bristles extending toward the anthers. The anthers tend to be captured within the bristles. As the tweezers are squeezed in place over the anthers, and then withdrawn from the flower, there is enough resistance caused by the bristles surrounding the anthers, to cause the anthers to break free from the filaments, but not enough resistance to cause the filaments to break from the flower.

In other preferred embodiments, the bristles have a length within the range of 1/32 to ¼ inch; the width of the tweezer arms is in the range of ⅜ to 1.5 inches; and the thickness of the foam layer is in the range of 1/16 to ¼ inch.

Other features and advantages of the invention will be apparent from the following description of a preferred embodiment and from the claims.

BRIEF DESCRIPTION OF THE DRAWINGS

FIG. 3A shows the lily before removal of the anthers; FIG. 3B shows the preferred embodiment after the tweezer arms have been squeezed down on the anthers; and FIG. 3C shows the lily with the anthers removed.

DESCRIPTION OF THE PREFERRED EMBODIMENT(S)

Figure 1:
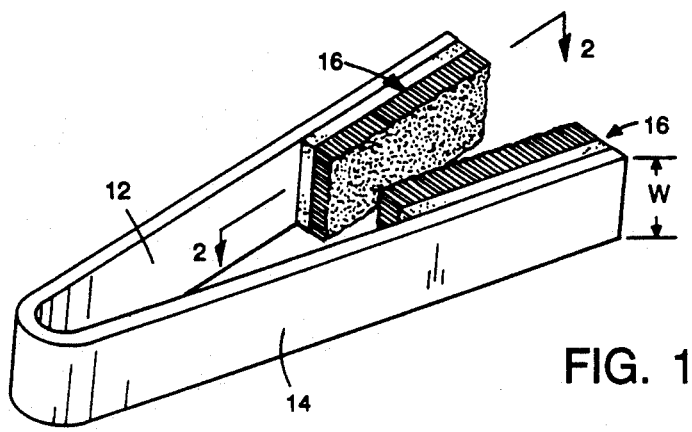
FIG. 1 is a perspective view of the preferred embodiment of the invention.
Figure 2:
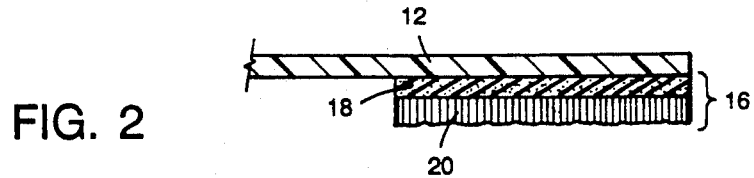
FIG. 2 is a cross-sectional view taken along 2—2 in FIG. 1, showing the foam and bristle layers at the ends of the tweezer.

Referring to FIGS. 1 and 2, the preferred embodiment has tweezer arms 12, 14 formed either by molding, or by bending a sheet of plastic. Any of various types of plastic material may be used. The tweezer arms are preferably ¾ inch in width W (FIG. 1), as this provides a good size for grasping all of the anthers and removing them in a single application. Smaller widths, but preferably more than ⅜ inch, may also be used, but tend to require multiple applications to remove all of the anthers of the flower. Wider widths can also be used, but the width is preferably less than 1.5 inches, as above 1.5 inches, the tweezer becomes difficult to insert into trumpet-shaped lilies, and generally awkward to operate. The overall length of the tweezer is important only for handling convenience; preferably it is in the range of 3 to 8 inches, and most preferably about 5.5 inches.

At the end of each tweezer arm there is a two-layer composite member 16 for contacting and removing the anthers of the lily. As shown in FIG. 2, the composite member 16 consists of an underlying foam layer 18 and bristle layer 20.

The foam layer is adhered by adhesive (e.g., contact cement) to the underlying tweezer arm 12. The foam layer is preferably ⅛ inch thick, but thickness anywhere from 1/16 to ¼ inch will function to provide the softness of grip that the foam serves to provide.

The bristle layer 20 consists of a multiplicity of short, polyester bristles oriented outwardly from the foam layer, and is adhered to the foam layer by an adhesive. Preferably, the composite material is manufactured by a flocking process in which the bristles are deposited by well-known flocking techniques into a layer of adhesive applied to the foam layer. A composite material that works well as members 16 is Mylofoam®, manufactured by American Converters, of Minneapolis, Minn., and distributed by Matco, of Minneapolis, Minn. Preferably the bristles are ⅛ inch long, but bristles anywhere from 1/32 to ½ inch in length should function to grip the anthers.

Figure 3A:
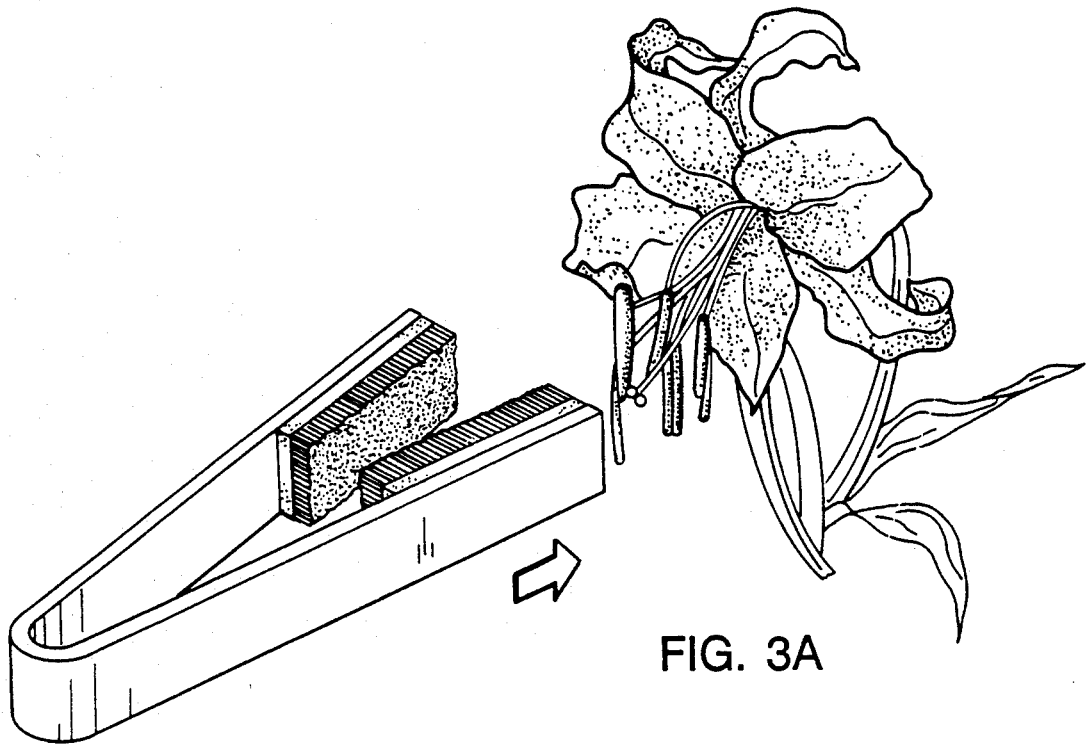
FIGS. 3A, 3B, and 3C show a lily in three stages.
Figure 3B:
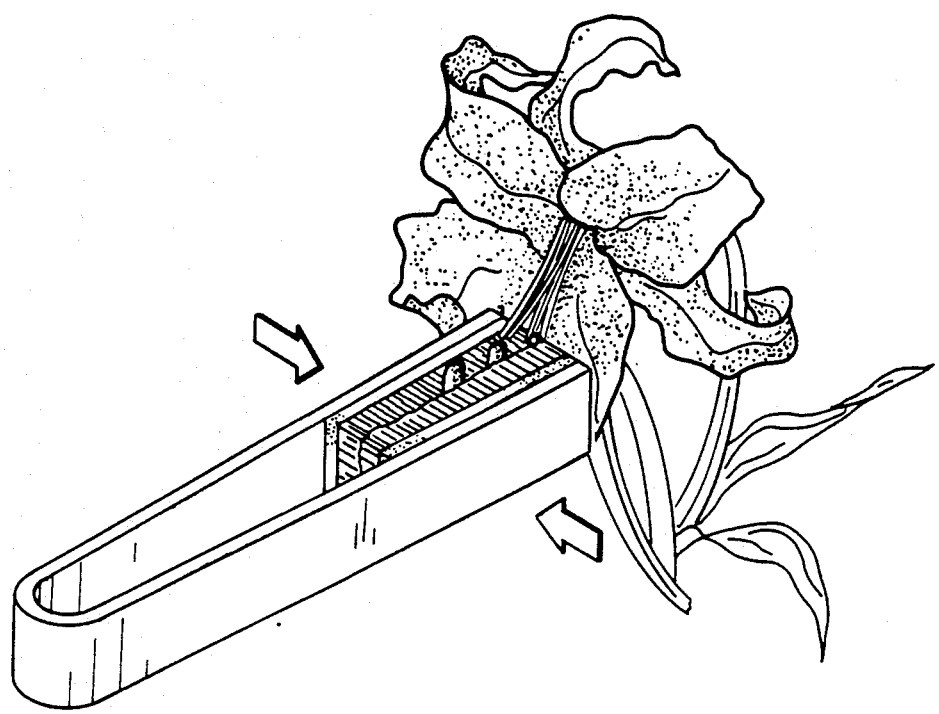
Figure 3C:
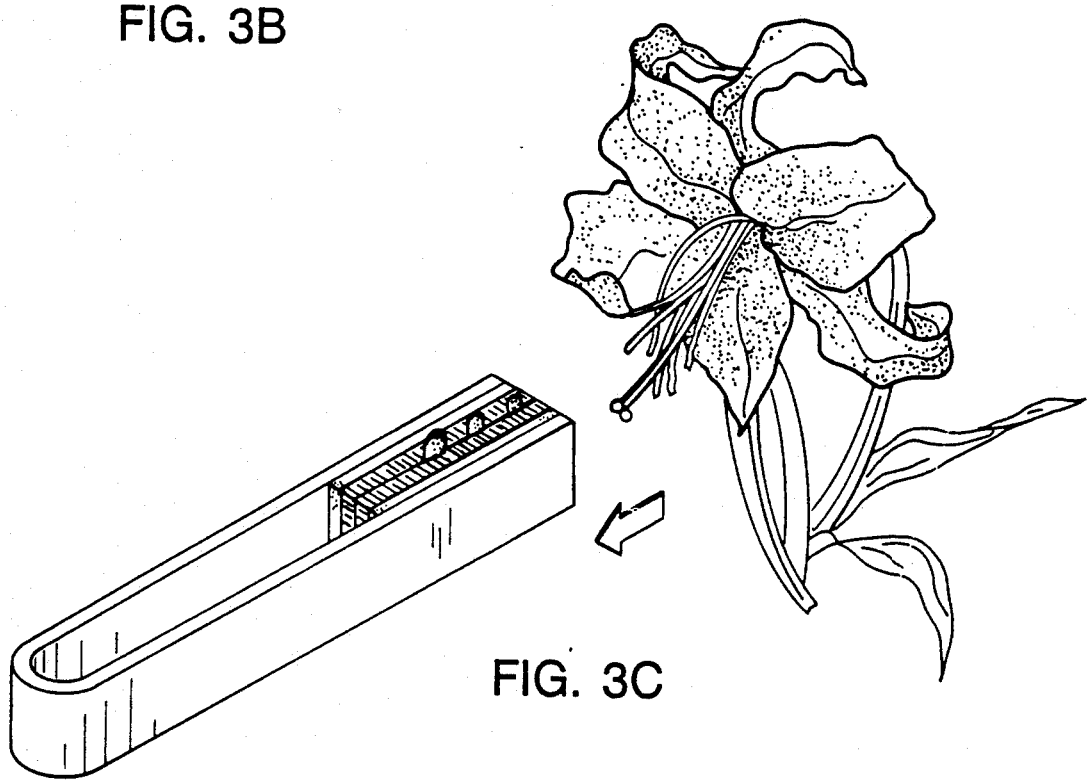

In use, as shown in the sequence of FIGS. 3A–3C, the tweezers are brought from the side (FIG. 3A) toward the filaments in a motion that captures all of the filaments (typically about five) of the lily between the ends of the tweezers (FIG. 3A). Then, the tweezer is withdrawn in a direction outward from the lily with the anthers captured. The anthers break away from the filaments, with the filaments left intact (FIG. 3C). The tweezers are then positioned over a waste receptacle, opened, and tapped against the receptacle to cause the pollen to fall into the receptacle. As pollen accumulates on the bristle layer, it can easily be cleaned simply by scraping the bristle layer across an edge. In this respect, the bristle layer is superior to simply having a foam layer for removal of the anthers, as pollen can tend to buildup on the foam layer and be more difficult to remove.

Other embodiments are within the following claims. E.g., other materials may be used for the composite member, e.g., a simple foam layer without the bristle layer. Other materials could be used for the bristle layer, and various foam materials could be used for the foam layer. Other materials than plastic could also be used for the tweezer body. FIGS. 3A–3C show use of the invention with an asiatic lily, but the invention is useful with other flowers, e.g., trumpet lilies such as the traditional Easter lily.

What is claimed is:

1. A tool for removing the pollen-covered anthers of a lily, said tool comprising:
    a body in the shape of a tweezers, said tweezers having two arms each having a free end extending in a longitudinal direction and said body being made of a material and said arms and body being configured so that said arms may be squeezed together in a transverse direction to bring the free ends of the tweezers arms together, and
    anther-contacting members adhered to the free end of each of said tweezers arms, said anther-contacting members comprising a multi-layer composite member adhered to each of said free ends of said tweezers arms,
    wherein said multi-layer composite members each include a foam layer supporting an outer bristle layer, said bristle layer containing a multiplicity of closely spaced bristles extending inwardly so that bristles from one layer contact bristles of the opposing composite member when said tweezers arms are squeezed together, and
    wherein said foam layer and bristle layers together provide sufficient softness and sufficient ability to grip the anthers to permit said anthers to be removed successfully in most instances without removal of the filaments supporting the anthers.

2. The tool of claim 1 wherein said bristle layer has bristles of a length within the range of 1.32 to ¼ inch.

3. The tool of claim 2 wherein the width of said tweezer arms is in the range of ⅜ to 1.5 inches.

4. The tool of claim 3 wherein the thickness of said foam layer is in the range of 1/16 to ¼ inch.

5. A method of removing the pollen-carrying anthers from a lily, said method comprising the steps of:
    (a) positioning over the anthers a tool comprising
        a body in the shape of a tweezers, said tweezers having two arms each having a free end in a longitudinal direction and said body being made of a material and said arm and body being configured so that said arms may be squeezed together in a transverse direction to bring the free ends of the tweezers arms together, and
        anther-contacting members adhered to the free end of each of said tweezers arms, said anther-contacting members comprising a
        multi-layer composite member adhered to each of said free ends of said tweezers arms,
        wherein said multi-layer composite members each include a foam layer supporting an outer bristle layer, said bristle layer containing a multiplicity of closely spaced bristles extending inwardly so that bristles from one layer contact bristles of the opposing composite member when said tweezers arms are squeezed together, and
        wherein said foam layer and bristle layers together provide sufficient softness and sufficient ability to grip the anthers to permit said anthers to be removed successfully in most instances without removal of the filaments supporting the anthers;
    (b) squeezing by hand said free ends to bring said anther-contacting members into contact with at least one of the anthers of the lily; and
    (c) moving the tool away from the lily, and thereby causing the anther grasped between the ends of the tweezers to break free from the filament supporting it without the filament breaking free from the lily.

6. The tool of claim 5 wherein said bristle layer has bristles of a length within the range of 1/32 to ¼ inch.

7. The tool of claim 6 wherein the width of said tweezer arms is in the range of ⅜ to 1.5 inches.

8. The tool of claim 7 wherein the thickness of said foam layer is in the range of 1/16 to 174 inch.

UNITED STATES PATENT AND TRADEMARK OFFICE
CERTIFICATE OF CORRECTION

PATENT NO. : 5,249,389

DATED : 10/5/93

INVENTOR(S) : Joseph S. Gallo

It is certified that error appears in the above-identified patent and that said Letters Patent is hereby corrected as shown below:

Cover page, item [56]: under FOREIGN PATENT DOCUMENTS, after "1758" delete "of".

Column 3, line 45, "1.32" should be --1/32--.

Column 4, line 9, after "end" insert, --extending--.

Column 4, line 44, "174" should be --1/4--.

Signed and Sealed this

Fifth Day of April, 1994

BRUCE LEHMAN

Attest:

*Attesting Officer*  *Commissioner of Patents and Trademarks*